(12) United States Patent
Rosinger et al.

(10) Patent No.: US 7,786,041 B2
(45) Date of Patent: Aug. 31, 2010

(54) SYNERGISTIC CROP PLANT-COMPATIBLE HERBICIDAL COMPOSITIONS COMPRISING HERBICIDES FROM THE GROUP OF THE BENZOYLCYCLOHEXANEDIONES

(75) Inventors: Christopher Rosinger, Hofheim (DE); Martin Hills, Idstein (DE); Stephan Müller, Waldems (DE); Thomas Wegmann, Langenfeld (DE)

(73) Assignee: Bayer CropScience AG (DE)

( * ) Notice: Subject to any disclaimer, the term of this patent is extended or adjusted under 35 U.S.C. 154(b) by 0 days.

(21) Appl. No.: 11/481,741

(22) Filed: Jul. 6, 2006

(65) Prior Publication Data

US 2007/0010398 A1    Jan. 11, 2007

(30) Foreign Application Priority Data

Jul. 7, 2005    (DE)    ........................ 10 2005 031 789

(51) Int. Cl.
*A01N 25/32*    (2006.01)
*A01N 43/64*    (2006.01)
*A01N 47/40*    (2006.01)
*A01N 37/00*    (2006.01)

(52) U.S. Cl. .................. 504/103; 504/133; 504/134; 504/141; 504/142

(58) Field of Classification Search ............. 504/103, 504/133, 134, 141, 142
See application file for complete search history.

(56) References Cited

U.S. PATENT DOCUMENTS

| | | | |
|---|---|---|---|
| 6,376,429 B1 * | 4/2002 | Van Almsick et al. | ....... 504/271 |
| 6,852,674 B2 | 2/2005 | Bickers et al. | |
| 6,872,691 B2 | 3/2005 | Schmitt et al. | |
| 6,884,757 B2 * | 4/2005 | Ziemer et al. | ............... 504/106 |
| 6,919,299 B2 | 7/2005 | Hacker et al. | |
| 7,202,196 B2 | 4/2007 | Fursch et al. | |

FOREIGN PATENT DOCUMENTS

| | | |
|---|---|---|
| WO | WO-02/085120 | 10/2002 |
| WO | WO-02/091831 | 11/2002 |
| WO | WO-03/020035 | 3/2003 |
| WO | WO-03/043422 | 3/2003 |
| WO | WO-03/043423 | 3/2003 |
| WO | WO-03/047340 | 6/2003 |
| ZA | 2004/3326 | 5/2003 |

* cited by examiner

*Primary Examiner*—Alton N Pryor
(74) *Attorney, Agent, or Firm*—Connolly Bove Lodge & Hutz LLP

(57) ABSTRACT

Synergistic crop plant-compatible herbicidal compositions comprising herbicides from the group of the benzoylcyclohexanediones Herbicidal compositions comprising
A) a compound from the group of the benzoylpyrazoles,
B) at least one further herbicide and
C) at least one safener
are described as herbicides which are active against monocotyledonous and/or dicotyledonous harmful plants.

Compared to the herbicides used on their own, these compositions have superior activity and at the same time high compatibility with crop plants.

10 Claims, No Drawings

SYNERGISTIC CROP PLANT-COMPATIBLE HERBICIDAL COMPOSITIONS COMPRISING HERBICIDES FROM THE GROUP OF THE BENZOYLCYCLOHEXANEDIONES

Synergistic crop plant-compatible herbicidal compositions comprising herbicides from the group of the benzoylcyclohexanediones The invention relates to the technical field of the crop protection compositions which can be used against unwanted vegetation and which comprise, as active compounds, a combination of at least two herbicides and one safener.

More specifically, it relates to herbicidal compositions comprising, as active compound, a herbicide from the group of the benzoylcyclohexanediones in combination with at least one further herbicide and a safener.

Herbicides from the abovementioned group of the benzoylcyclohexanediones are known from numerous documents. Thus, for example, U.S. Pat. No. 6,376,429 describes benzoylcyclohexanediones having herbicidal action.

However, in practice, the use of the benzoylcyclohexanediones known from these publications is frequently associated with disadvantages. Thus, the herbicidal activity of the known compounds is not always sufficient, or, if the herbicidal activity is sufficient, then undesired damage to the useful plants is observed.

The effectiveness of herbicides depends inter alia on the type of herbicide used, its application rate, the formulation, the harmful plants to be controlled in each case, climatic and soil conditions, etc. A further criterion is the persistency or the rate at which the herbicide is degraded. Changes in the susceptibility of harmful plants to an active compound which may occur on prolonged use or in specific geographical regions may also have to be taken into account. Such changes manifest themselves by a more or less pronounced loss in activity and can only be compensated to a limited extent by higher herbicide application rates.

One way to improve the application profile of a herbicide may be the combination of the active compound with one or more other active compounds. Combinations of herbicidally effective benzoyl derivatives with other herbicides are known from WO 03/043422 and WO 03/043423. However, when a number of active compounds are applied in combination, it is not uncommon for phenomena of physical and biological incompatibility to occur, for example insufficient stability of a joint formulation, decomposition of an active compound or antagonism of the active compounds. What is desired are, in contrast, active compound combinations having a favorable activity profile, high stability and, if possible, synergistically enhanced activity, thus permitting the application rate to be reduced, compared with the individual application of the active compounds to be combined.

Owing to the large number of possible influencing factors, there is virtually no individual active compound which has all the desired properties for different requirements, in particular with respect to the species of harmful plants and the climatic zones. Furthermore, there is the permanent object to achieve the effect using more and more reduced herbicide application rates. A lower application rate reduces not only the amount of active compound required for the application, but generally also reduces the amount of formulation auxiliaries required. Both reduce the economic expense and improve the ecological compatibility of the herbicide treatment.

As is the case with many other herbicidally active compounds, benzoylcyclohexanediones, too, in particular in combination with other herbicides, are not always sufficiently compatible with (i.e. not selective enough in) some important crop plants, such as corn, rice or cereal, so that their use is highly restricted. As a consequence, in some crops, they cannot be employed or can only be employed at application rates which are so low that the desired broad herbicidal activity against harmful plants is not ensured. Specifically, many of the herbicides mentioned cannot be employed entirely selectively against harmful plants in corn, rice, cereal, sugar cane and some other crops.

To overcome these disadvantages, it is known to employ herbicidal active compounds in combination with what is known as a safener or antidote. Thus, for example, U.S. Pat. No. 6,884,757 describes various combinations of benzoylcyclohexanediones with a large number of safeners.

A safener is understood as meaning a compound which compensates for, or reduces, the phytotoxic properties of a herbicide with regard to useful plants, without substantially reducing the herbicidal activity against harmful plants.

Finding a safener for a specific group of herbicides remains a difficult task since the mechanisms by which a safener reduces the harmful action of herbicides are not known in detail. The fact that a compound in combination with a specific herbicide acts as a safener therefore allows no conclusions to be drawn as to whether such a compound also has a safener action with other groups of herbicides. Thus, it has emerged when safeners are used for protecting the useful plants from herbicide damage that the safeners may still exhibit certain disadvantages in many cases. These include:

the safener reduces the activity of the herbicides against the harmful plants,
the useful-plant-protecting properties are insufficient,
the spectrum of the useful plants in which the safener/herbicide is to be employed is not sufficiently wide in combination with a given herbicide,
a given safener cannot be combined with a sufficiently large number of herbicides.

It is an object of the present invention to provide herbicidal compositions having properties which are improved compared to the prior art.

The invention provides selected herbicidal compositions comprising an effective amount of A) the herbicide of the formula A and its agriculturally customary salts (component A),

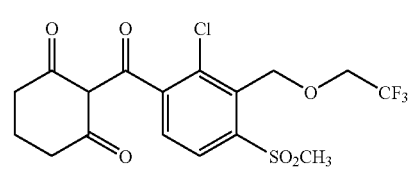

B) at least one herbicide (component B) from the group comprising the active compounds atrazine (B1), bromoxynil (B2), dicamba (B3), flufenacet (B4), foramsulfuron (B5), glufosinate (B6), glyphosate (B7), nicosulfuron (B8), terbuthylazine (B9), metolachlor (B10), and C) an antidotically effective amount of at least one safener (component C) from the group comprising the active compounds isoxadifen-ethyl (C1), cloquintocet-mexyl (C2), N-({4-[(cyclopropylamino)-carbonyl]phenyl}sulfonyl)-2-methoxybenzamide (C3), where these compositions comprise the components A, B and C in a weight ratio of x:y:z in which x, y and z in each case independently of one another may assume values of from 1 to 200, preferably from 1 to 100.

Hereinbelow, the terms "component A", "herbicide A" and "active compound A" are to be understood as meaning the same. This applies analogously to the terms "component B", "herbicide B" and "active compound B" and also to "component C", "safener C" and "active compound C".

The herbicide A is known, for example, from U.S. Pat. No. 6,376,429. The safener C3 is known, for example, from U.S. Pat. No. 6,251,827. The disclosure of the abovementioned publications is incorporated into the present description by way of reference. The chemical structures of the other active compounds referred to above by their common names are known, for example, from "The Pesticide Manual" 13th edition, 2003, British Crop Protection Council. If, in the context of this description, the short form of the common name of an active compound is used, this embraces in each case all customary derivatives, such as the esters and salts, and isomers, in particular optical isomers, especially the commercial form or forms. If the common name refers to an ester or salt, this also includes in each case all other customary derivatives, such as other esters and salts, the free acids and neutral compounds, and isomers, in particular optical isomers, especially the commercial form or forms. The given chemical compound names refer to at least one of the compounds embraced by the common name, frequently to a preferred compound.

In a preferred embodiment, the herbicidal compositions according to the invention are synergistically active and at the same time highly compatible with crop plants. The synergistic actions and the high compatibility with crop plants can be observed, for example, when the components A, B and C are applied together; however, they can frequently also be observed when the active compounds are applied at different times (splitting). It is also possible to apply the individual herbicides and safeners or the herbicide/safener combinations in a plurality of portions (sequential application), for example pre-emergence applications followed by post-emergence applications or early post-emergence applications followed by medium or late post-emergence applications. Preference is given here to the joint or almost simultaneous application of the active compounds of the herbicide combination according to the invention.

The synergistic effects permit a reduction of the application rates of the individual active compounds, a higher efficacy at the same application rate, the control of species which are as yet uncontrolled (gaps), an extension of the period of application and/or a reduction in the number of individual applications required and—as a result for the user—weed control systems which are more advantageous economically and ecologically.

The invention also encompasses herbicidal compositions which, in addition to the components A, B and C, also comprise one or more further agrochemically active compounds of a different structure, such as herbicides, insecticides, fungicides or safeners. The preferred conditions illustrated above and below also apply to these herbicidal compositions.

The invention also encompasses herbicidal compositions which, in addition to the components A, B and C, also comprise fertilizers, such as ammonium sulfate, ammonium nitrate, urea, potassium nitrate and mixtures thereof. The preferred conditions illustrated above and below also apply to these herbicidal compositions.

The invention furthermore also embraces herbicidal compositions which, in addition to the components A, B and C, also comprise adjuvants, such as emulsifiers, dispersants, mineral and vegetable oils and mixtures thereof. The preferred conditions illustrated above and below also apply to these herbicidal compositions.

Of particular interest are herbicidal compositions comprising
A) the herbicide A,
B) at least one herbicide (component B) from the group comprising the active compounds atrazine (B1), bromoxynil (B2), dicamba (B3), flufenacet (B4), foramsulfuron (B5), glufosinate (B6), glyphosate (B7), nicosulfuron (B8), terbuthylazine (B9), and
C) an antidotically effective amount of at least one safener (component C) from the group comprising the active compounds isoxadifen-ethyl (C1), cloquintocet-mexyl (C2), N-({4-[(cyclopropylamino)carbonyl]phenyl}sulfonyl)-2-methoxybenzamide (C3).

Of particular interest are herbicidal compositions comprising one or more of the following combinations of three compounds (A+B+C):
(A+B1+C1), (A+B2+C1), (A+B3+C1), (A+B4+C1), (A+B5+C1),
(A+B6+C1), (A+B7+C1), (A+B8+C1), (A+B9+C1), (A+B10+C1),
(A+B1+C2), (A+B2+C2), (A+B3+C2), (A+B4+C2), (A+B5+C2),
(A+B6+C2), (A+B7+C2), (A+B8+C2), (A+B9+C2), (A+B10+C2),
(A+B1+C3), (A+B2+C3), (A+B3+C3), (A+B4+C3), (A+B5+C3),
(A+B6+C3), (A+B7+C3), (A+B8+C3), (A+B9+C3), (A+B10+C3).

Of particular interest are also herbicidal compositions comprising one or more of the following combinations of three compounds (A+B+C):
(A+B1+C1), (A+B2+C1), (A+B3+C1), (A+B4+C1), (A+B5+C1),
(A+B6+C1), (A+B7+C1), (A+B8+C1), (A+B9+C1),
(A+B1+C2), (A+B2+C2), (A+B3+C2), (A+B4+C2), (A+B5+C2),
(A+B6+C2), (A+B7+C2), (A+B8+C2), (A+B9+C2),
(A+B1+C3), (A+B2+C3), (A+B3+C3), (A+B4+C3), (A+B5+C3),
(A+B6+C3), (A+B7+C3), (A+B8+C3), (A+B9+C3).

In a further preferred embodiment, the herbicidal compositions according to the invention comprise the herbicide A, two different components B and one safener C.

Among these, particular preference is given to herbicidal compositions comprising one or more of the following combinations of four compounds (A+B+B+C):
(A+B1+B2+C1), (A+B1+B3+C1), (A+B1+B4+C1), (A+B1+B5+C1),
(A+B1+B6+C1), (A+B1+B7+C1), (A+B1+B8+C1), (A+B1+B9+C1),
(A+B1+B10+C1);
(A+B1+B2+C2), (A+B1+B3+C2), (A+B1+B4+C2), (A+B1+B5+C2),
(A+B1+B6+C2), (A+B1+B7+C2), (A+B1+B8+C2), (A+B1+B9+C2),
(A+B1+B10+C2);
(A+B1+B2+C3), (A+B1+B3+C3), (A+B1+B4+C3), (A+B1+B5+C3),
(A+B1+B6+C3), (A+B1+B7+C3), (A+B1+B8+C3), (A+B1+B9+C3),
(A+B1+B10+C3),
(A+B2+B3+C1), (A+B2+B4+C1), (A+B2+B5+C1), (A+B2+B6+C1),
(A+B2+B7+C1), (A+B2+B8+C1), (A+B2+B9+C1), (A+B2+B10+C1);
(A+B2+B3+C2), (A+B2+B4+C2), (A+B2+B5+C2), (A+B2+B6+C2), (A+B2+B7+C2), (A+B2+B8+C2), (A+B2+B9+C2), (A+B2+B10+C2);
(A+B2+B3+C3), (A+B2+B4+C3), (A+B2+B5+C3), (A+B2+B6+C3),
(A+B2+B7+C3), (A+B2+B8+C3), (A+B2+B9+C3), (A+B2+B10+C3),
(A+B3+B4+C1), (A+B3+B5+C1), (A+B3+B6+C1), (A+B3+B7+C1),
(A+B3+B8+C1), (A+B3+B9+C1), (A+B3+B10+C1);
(A+B3+B4+C2), (A+B3+B5+C2), (A+B3+B6+C2), (A+B3+B7+C2),
(A+B3+B8+C2), (A+B3+B9+C2), (A+B3+B10+C2);
(A+B3+B4+C3), (A+B3+B5+C3), (A+B3+B6+C3), (A+B3+B7+C3),
(A+B3+B8+C3), (A+B3+B9+C3), (A+B3+B10+C3),
(A+B4+B5+C1), (A+B4+B6+C1), (A+B4+B7+C1), (A+B4+B8+C1),
(A+B4+B9+C1), (A+B4+B10+C1);
(A+B4+B5+C2), (A+B4+B6+C2), (A+B4+B7+C2), (A+B4+B8+C2),
(A+B4+B9+C2), (A+B4+B10+C2);
(A+B4+B5+C3), (A+B4+B6+C3), (A+B4+B7+C3), (A+B4+B8+C3),
(A+B4+B9+C3), (A+B4+B10+C3),
(A+B5+B6+C1), (A+B5+B7+C1), (A+B5+B8+C1), (A+B5+B9+C1),
(A+B5+B10+C1);
(A+B5+B6+C2), (A+B5+B7+C2), (A+B5+B8+C2), (A+B5+B9+C2),
(A+B5+B10+C2);
(A+B5+B6+C3), (A+B5+B7+C3), (A+B5+B8+C3), (A+B5+B9+C3),
(A+B5+B10+C3),
(A+B6+B7+C1), (A+B6+B8+C1), (A+B6+B9+C1), (A+B6+B10+C1);
(A+B6+B7+C2), (A+B6+B8+C2), (A+B6+B9+C2), (A+B6+B10+C2);
(A+B6+B7+C3), (A+B6+B8+C3), (A+B6+B9+C3), (A+B6+B10+C3),
(A+B7+B8+C1), (A+B7+B9+C1), (A+B7+B10+C1);
(A+B7+B8+C2), (A+B7+B9+C2), (A+B7+B10+C2);
(A+B7+B8+C3), (A+B7+B9+C3), (A+B7+B10+C3),
(A+B8+B9+C1), (A+B8+B10+C1);
(A+B8+B9+C2), (A+B8+B10+C2);
(A+B8+B9+C3), (A+B8+B10+C3).

Particular preference is also given to herbicidal compositions comprising one or more of the following combinations of four compounds (A+B+B+C):

(A+B1+B2+C1), (A+B1+B3+C1), (A+B1+B4+C1), (A+B1+B5+C1),
(A+B1+B6+C1), (A+B1+B7+C1), (A+B1+B8+C1), (A+B1+B9+C1),
(A+B1+B2+C2), (A+B1+B3+C2), (A+B1+B4+C2), (A+B1+B5+C2),
(A+B1+B6+C2), (A+B1+B7+C2), (A+B1+B8+C2), (A+B1+B9+C2),
(A+B1+B2+C3), (A+B1+B3+C3), (A+B1+B4+C3), (A+B1+B5+C3),
(A+B1+B6+C3), (A+B1+B7+C3), (A+B1+B8+C3), (A+B1+B9+C3),
(A+B2+B3+C1), (A+B2+B4+C1), (A+B2+B5+C1), (A+B2+B6+C1),
(A+B2+B7+C1), (A+B2+B8+C1), (A+B2+B9+C1),
(A+B2+B3+C2), (A+B2+B4+C2), (A+B2+B5+C2), (A+B2+B6+C2),
(A+B2+B7+C2), (A+B2+B8+C2), (A+B2+B9+C2),
(A+B2+B3+C3), (A+B2+B4+C3), (A+B2+B5+C3), (A+B2+B6+C3),
(A+B2+B7+C3), (A+B2+B8+C3), (A+B2+B9+C3),
(A+B3+B4+C1), (A+B3+B5+C1), (A+B3+B6+C1), (A+B3+B7+C1),
(A+B3+B8+C1), (A+B3+B9+C1),
(A+B3+B4+C2), (A+B3+B5+C2), (A+B3+B6+C2), (A+B3+B7+C2),
(A+B3+B8+C2), (A+B3+B9+C2),
(A+B3+B4+C3), (A+B3+B5+C3), (A+B3+B6+C3), (A+B3+B7+C3),
(A+B3+B8+C3), (A+B3+B9+C3),
(A+B4+B5+C1), (A+B4+B6+C1), (A+B4+B7+C1), (A+B4+B8+C1),
(A+B4+B9+C1),
(A+B4+B5+C2), (A+B4+B6+C2), (A+B4+B7+C2), (A+B4+B8+C2),
(A+B4+B9+C2),
(A+B4+B5+C3), (A+B4+B6+C3), (A+B4+B7+C3), (A+B4+B8+C3),
(A+B4+B9+C3),
(A+B5+B6+C1), (A+B5+B7+C1), (A+B5+B8+C1), (A+B5+B9+C1),
(A+B5+B6+C2), (A+B5+B7+C2), (A+B5+B8+C2), (A+B5+B9+C2),
(A+B5+B6+C3), (A+B5+B7+C3), (A+B5+B8+C3), (A+B5+B9+C3),
(A+B6+B7+C1), (A+B6+B8+C1), (A+B6+B9+C1),
(A+B6+B7+C2), (A+B6+B8+C2), (A+B6+B9+C2),
(A+B6+B7+C3), (A+B6+B8+C3), (A+B6+B9+C3),
(A+B7+B8+C1), (A+B7+B9+C1),
(A+B7+B8+C2), (A+B7+B9+C2),
(A+B7+B8+C3), (A+B7+B9+C3),
(A+B8+B9+C1),
(A+B8+B9+C2),
(A+B8+B9+C3).

For the herbicidal compositions according to the invention, application rates in the range from 1 to 2000 g, preferably from 10 to 1000 g, particularly preferably from 10 to 300 g, of active ingredient per hectare (ai/ha) of the component A and from 1 to 2000 g, preferably from 1 to 1000 g, particularly preferably from 5 to 500 g, of the component B and from 1 to 1000 g, preferably from 1 to 500 g, particularly preferably from 5 to 250 g, of the component C are generally required.

The weight ratios of the components A to B on the one hand and (A+B) to C on the other hand can be varied within wide ranges. The ratio of the components A to B is preferably in the range from 1:100 to 100:1, particularly preferably in the range from 1:50 to 50:1, especially in the range from 1:20 to 20:1. The ratio of the components (A+B) to C is preferably in the range from 1:10 to 50:1, in particular in the range from 1:5 to 20:1. The ranges mentioned above also apply to the case where the herbicidal compositions according to the invention comprise more than one component B and/or component C. In this case, the numbers mentioned apply to the sum of the individual values of the components B or C.

Optimum weight ratios may depend on the particular field of application, on the weed spectrum and on the active compound combination used and can be determined in preliminary experiments.

The compositions according to the invention can be employed for the selective control of annual and perennial monocotyledonous and dicotyledonous harmful plants in crops of cereals (for example barley, oats, rye, wheat), corn and rice and in crops of transgenic useful plants or crops of useful plants selected by classical means which are resistant to the active compounds A and B. Likewise, they can be employed for controlling unwanted harmful plants in plantation crops such as oil palm, coconut palm, Indian-rubber tree, citrus, pineapple, cotton, coffee, cocoa and the like, and also in fruit production and viticulture. Owing to their good compatibility, they are particularly suitable for use in cereals and corn, especially corn.

The compositions according to the invention act against a broad spectrum of weeds. They are suitable, for example, for controlling annual and perennial harmful plants such as, for example, from the species *Abutilon, Alopecurus, Avena, Chenopodium, Cynoden, Cyperus, Digitaria, Echinochloa, Elymus, Galium, Ipomoea, Kochia, Lamium, Matricaria, Polygonum, Scirpus, Setaria, Sorghum, Veronica, Viola* and *Xanthium.*

A further advantage of the compositions according to the invention is their excellent action against many harmful plants which have now become resistant to sulfonylureas, such as, for example, *Kochia.*

The invention also provides a method for controlling unwanted vegetation, which comprises applying the herbicide A and one or more herbicides B and one or more safeners C to the harmful plants, to parts of the harmful plants or to the area under cultivation.

The herbicidal compositions according to the invention are also distinguished by the fact that the effective dosages of the components A and B used in the combinations are reduced with respect to an individual dosage, so that it is possible to reduce the required active compound application rates (synergistic effect). At the same time, the compatibility with crop plants is more pronounced by the presence of the safener (C) than in the case of a combination of the safener C with the herbicide A or a herbicide B. The synergistic effects permit the application rate to be reduced, a broader spectrum of broad-leaved weeds and weed grasses to be controlled, a more rapid onset of the herbicidal action, a longer persistency, better control of the harmful plants by only one application, or few applications, and widening of the period of time within which the product can be used. These properties are required in weed control practice to keep agricultural crops free from unwanted competing plants and thus to ensure and/or to increase quality and quantity of the yields. These novel combinations markedly surpass the prior art with respect to the described properties.

The herbicidal compositions according to the invention can either be present as mixed formulations of the herbicides A and B and the safener C, if appropriate together with other customary formulation auxiliaries, which mixed formulations are then applied in the usual manner in the form of a dilution with water, or else they can be prepared in the form of so-called tank mixes by joint dilution with water or with aqueous solutions of fertilizers, for example ammonium nitrate or ammonium sulfate, of the components which are formulated separately, or partly separately.

The herbicidal compositions according to the invention can be formulated in various ways, depending on the prevailing biological and/or physicochemical parameters. Suitable general possibilities for formulations are, for example: wettable powders (WP), emulsifiable concentrates (EC), aqueous solutions (SL), emulsions (EW) such as oil-in-water and water-in-oil emulsions, sprayable solutions or emulsions, oil suspension concentrate (SC), oil-or water-based dispersions, suspoemulsions, dusts (DP), seed dressing products, granules for soil application or for broadcasting or water-dispersible granules (WG), water-dispersible granules (WDG), water-emulsifiable granules (WEG), ULV formulations, microcapsules or waxes.

The individual types of formulation are known in principle and are described, for example, in: Winnacker-Küchler, "Chemische Technologie" [Chemical Technology], Vol. 7, C. Hauser Verlag Munich, 4th Ed. 1986; van Valkenburg, "Pesticides Formulations", Marcel Dekker N.Y., 1973; K. Martens, "Spray Drying Handbook", 3rd Ed. 1979, G. Goodwin Ltd. London. The formulation auxiliaries required, such as inert materials, surfactants, solvents and other additives, are also known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976; Winnacker-Küchler, "Chemische Technologie" [Chemical Technology], Vol. 7, C. Hauser Verlag Munich, 4th Ed. 1986.

Based on these formulations, it is also possible to prepare combinations with other pesticidally active substances, such as other herbicides, fungicides or insecticides, and also safeners, fertilizers and/or growth regulators, for example in the form of a ready mix or tank mix.

Wettable powders are preparations which are uniformly dispersible in water and which, besides the active compound, also comprise ionic or nonionic surfactants (wetting agents, dispersants), for example polyethoxylated alkylphenols, polyethoxylated fatty alcohols or fatty amines, alkanesulfonates or alkylbenzene-sulfonates, sodium lignosulfonate, sodium 2,2'-dinaphthylmethane-6,6'-disulfonate, sodium dibutyinaphthalenesulfonate or else sodium oleoylmethyltaurinate, in addition to a diluent or an inert substance.

Emulsifiable concentrates are prepared by dissolving the active compound in an organic solvent, for example butanol, cyclohexanone, dimethylformamide, xylene or else higher-boiling aromatics or hydrocarbons, with the addition of one or more ionic or nonionic surfactants (emulsifiers). Examples of emulsifiers which can be used are: calcium alkylarylsulfonates, such as calcium dodecylbenzenesulfonate, or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxyethylene sorbitol esters.

Dusts are obtained by grinding the active compound with finely divided solid materials, for example talc, natural clays, such as kaolin, bentonite and pyrophyllite, or diatomaceous earth.

Granules can be prepared either by spraying the active compound onto absorptive, granulated inert material, or by applying active compound concentrates to the surface of carriers, such as sand, kaolinite or granulated inert material, with the aid of binders, for example polyvinyl alcohol, sodium polyacrylate or else mineral oils. Suitable active compounds can also be granulated in the manner customary for the preparation of fertilizer granules, if desired as a mixture with fertilizers. Water-dispersible granules are, in general, prepared by processes such as spray-drying, fluidized-bed granulation, disk granulation, mixing using high-speed mixers, and extrusion without solid inert material.

The agrochemical preparations generally comprise from 0.1 to 99 percent by weight, in particular from 0.2 to 95% by weight, of components A, B and C, the following concentrations being customary, depending on the type of formulation:

in wettable powders, the active compound concentration is, for example, approximately 10 to 95% by weight, the remainder to 100% by weight being composed of customary formulation components. In the case of emulsifiable concentrates, the active compound concentration can be, for example, from 5 to 80% by weight. Formulations in the form of dusts in most cases comprise from 5 to 20% by weight of active compound, sprayable solutions approximately 0.2 to 25% by weight of active compound. In the case of granules, such as dispersible granules, the active compound content depends partly on whether the active compound is in liquid or solid form and on which granulation auxiliaries and fillers are used. In general, the content in the water-dispersible granules amounts to between 10 and 90% by weight. In addition, the active compound formulations mentioned comprise, if appropriate, the tackifiers, wetting agents, dispersants, emulsifiers, preservatives, antifreeze agents, solvents, fillers, colorants, carriers, antifoams, evaporation inhibitors and pH or viscosity regulators which are customary in each case.

For use, the formulations, which are in commercially available form, are, if appropriate, diluted in a customary manner, for example using water in the case of wettable powders, emulsifiable concentrates, dispersions and water-dispersible granules. Preparations in the form of dusts, soil granules, granules for spreading and sprayable solutions are conventionally not diluted any further with other inert substances prior to use.

The active compounds can be applied to the plants, to parts of plants, to plant seeds or to the area under cultivation (tilled soil), preferably to the green plants and parts of the plants and, if desired, additionally to the tilled soil.

A possible use is the joint application of the active compounds in the form of tank mixes, where the concentrated formulations of the individual active compounds, in the form of their optimal formulations, are mixed jointly with water in the tank or with aqueous solutions of fertilizer, such as ammonium nitrate and ammonium sulfate for example, and the spray mixture obtained is applied.

A joint herbicidal formulation of the herbicidal compositions according to the invention has the advantage that it can be applied more easily because the amounts of the components have already been adjusted with respect to one another to the correct ratio. Moreover, the auxiliaries of the formulation can be selected to suit each other in the best possible way, while a tank mix of various formulations may result in undesirable combinations of auxiliaries.

A. FORMULATION EXAMPLES a) A dust (WP) is obtained by mixing 10 parts by weight of an active compound/active compound mixture and 90 parts by weight of talc as inert substance and comminuting the mixture in a hammer mill.

b) A wettable powder (WG) which is readily dispersible in water is obtained by mixing 25 parts by weight of an active compound/active compound mixture, 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.

c) A dispersion concentrate which is readily dispersible in water is obtained by mixing 20 parts by weight of an active compound/active compound mixture with 6 parts by weight of alkylphenol polyglycol ether (Triton X 207), 3 parts by weight of isotridecanol polyglycol ether (8 EO) and 71 parts by weight of paraffinic mineral oil (boiling range for example approximately 255 to 277° C.) and grinding the mixture in a ball mill to a fineness of below 5 microns.

d) An emulsifiable concentrate (EC) is obtained from 15 parts by weight of an active compound/active compound mixture, 75 parts by weight of cyclohexanone as solvent and 10 parts by weight of ethoxylated nonylphenol as emulsifier.

e) Water-dispersible granules are obtained by mixing
    75 parts by weight of an active compound/active compound mixture,
    10 parts by weight of calcium lignosulfonate,
    5 parts by weight of sodium lauryl sulfate,
    3 parts by weight of polyvinyl alcohol and
    7 parts by weight of kaolin,
grinding the mixture in a pinned-disk mill and granulating the powder in a fluidized bed by spraying on water as granulation liquid.

f) Water-dispersible granules are also obtained by homogenizing and precomminuting, in a colloid mill,
    25 parts by weight of an active compound/active compound mixture,
    5 parts by weight of sodium 2,2'-dinaphthylmethane-6,6'-disulfonate,
    2 parts by weight of sodium oleoylmethyltaurinate,
    1 part by weight of polyvinyl alcohol,
    17 parts by weight of calcium carbonate and
    50 parts by weight of water,
subsequently grinding the mixture in a bead mill and atomizing and drying the resulting suspension in a spray tower by means of a single-substance nozzle.

B. BIOLOGICAL EXAMPLES

1. Herbicidal Post-Emergence Action

Seeds of monocotyledonous and dicotyledonous weed and crop plants are placed into sandy loam in wood fiber pots or in plastic pots, covered with soil and cultivated in a greenhouse, including during the vegetation period outdoors outside of the greenhouse, under good growth conditions. 2-3 weeks after sowing, the test plants are treated at the one- to three-leaf stage. The test compounds, formulated as wettable powders (WP) or liquid (EC) are, in various dosages with a water application rate of 300 l/ha (converted), with added wetting agent (0.2 to 0.3%), sprayed onto the plants and the surface of the soil. 3 to 4 weeks after the treatment of the test plants, the effect of the preparations is rated visually in comparison to untreated controls (herbicidal effect in percent (%): 100% effect=plants have died, 0% effect=like control plants).

The surprisingly good activity of the herbicidal compositions according to the invention was confirmed in numerous comparative tests. To this end, in a first test series, the herbicidal activity of mixtures, known from the prior art, comprising herbicide A and herbicide B were compared to the herbicidal activity of a composition according to the invention comprising in each case the same herbicides and a safener. Surprisingly, it was found that the herbicidal activity was enhanced further by the safener; see Tables 1 to 4.

The abbreviations denote:

| BRAPP | *Brachiaria platyphylla* | POLCO | *Fallopia convolvulus* |
|---|---|---|---|
| SETFA | *Setaria faberi* | SETVI | *Setaria viridis* |
| SORHA | *Sorghum halepense* | | |

TABLE 1

| | Post-emergence action | | |
| --- | --- | --- | --- |
| | Dosage | Herbicidal action | |
| Compound | [g of a.i./ha] | BRAPP | SORHA |
| A + B1 | 200 + 200 | 85% | 65% |
| A + B1 + C1 | 200 + 200 + 100 | 90% | 83% |

TABLE 2

| | Post-emergence action | | |
| --- | --- | --- | --- |
| | Dosage | Herbicidal action | |
| Compound | [g of a.i./ha] | BRAPP | SETVI |
| A + B3 | 200 + 200 | 70% | 68% |
| A + B3 + C1 | 200 + 200 + 100 | 85% | 70% |

TABLE 3

| | Post-emergence action | | |
| --- | --- | --- | --- |
| | Dosage | Herbicidal action | |
| Compound | [g of a.i./ha] | SETFA | SORHA |
| A + B2 | 200 + 200 | 88% | 68% |
| A + B2 + C1 | 200 + 200 + 100 | 90% | 70% |

TABE 4

| | Post-emergence action | | |
| --- | --- | --- | --- |
| | Dosage | Herbicidal action | |
| Compound | [g of a.i./ha] | SORHA | POLCO |
| A + B9 | 200 + 200 | 88% | 90% |
| A + B9 + C1 | 200 + 200 + 100 | 93% | 93% |

In a second test series, the herbicidal action and the damage to corn of the compositions according to the invention (A+Bx+C1) was compared to that of the herbicide alone (A) and to that of a herbicidal composition (A+C1) known from the prior art. Surprisingly, it was found that the herbicidal compositions according to the invention not only have slightly higher herbicidal activity but at the same time cause less damage to the crop plant; see Table 5, in which the herbicidal action is stated as the mean value of the herbicidal actions against the harmful plants *Abutilon theophrasti, Ambrosia elatior, Digitaria sanguinalis, Echinochloa crus galli, Pharbitis purpureum, Fallopia convolvulus, Setaria faberi, Setaria viridis, Sorghum halepense, Brachiaria platyphylla*.

TABLE 5

| | Post-emergence action | | | |
| --- | --- | --- | --- | --- |
| Compound | Dosage [g of a.i./ha] | Herbicidal action | Damage to corn | Reduction of the damage to corn |
| A | 200 | 86% | 11% | — |
| A + C1 | 200 + 100 | 83% | 6% | −45% |
| A + B1 + C1 | 200 + 200 + 100 | 93% | 0% | −100% |
| A + B2 + C1 | 200 + 200 + 100 | 87% | 4% | −64% |
| A + B3 + C1 | 200 + 200 + 100 | 84% | 3% | −73% |
| A + B9 + B10 + C1 | 200 + 200 + 200 + 100 | 94% | 4% | −64% |

The invention claimed is:

1. A herbicidal composition, comprising an effective amount of
   A) the herbicide of the formula A and its agriculturally customary salts (component A),

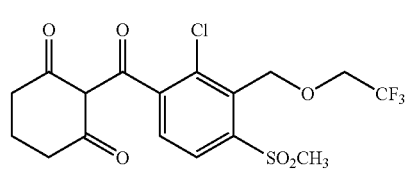

A

B) at least one herbicide (component B) selected from the group consisting of atrazine, bromoxynil, dicamba, terbuthylazine, and metolachlor, and
   C) an antidotically effective amount of isoxadifen-ethyl (component C).

2. The herbicidal composition as claimed in claim 1, which comprises the components A, B and C in a weight ratio of x:y:z in which x, y and z in each case independently of one another assume values of from 1 to 200.

3. The herbicidal composition as claimed in claim 1, in which x, y and z in each case independently of one another assume values of from 1 to 100.

4. The herbicidal composition as claimed in claim 1, additionally comprising formulating agents customary in crop protection.

5. The herbicidal composition as claimed in claim 1, additionally comprising fertilizers.

6. The herbicidal composition as claimed in claim 1, additionally comprising adjuvants.

7. A method for controlling unwanted vegetation, which comprises applying the components A, B and C as defined in claim 1 jointly or separately to harmful plants, to parts of the harmful plants, to harmful plant seeds or to an area under cultivation.

8. The method as claimed in claim 7 for selective control of the harmful plants in crops of useful plants.

9. The method as claimed in claim 7 for control of the harmful plants in crops of monocotyledonous plants.

10. The method as claimed in claim 8, wherein the useful plants are crop plants that are genetically modified or have been obtained by mutation selection.

\* \* \* \* \*